(12) United States Patent
Agarwal et al.

(10) Patent No.: US 12,318,073 B2
(45) Date of Patent: Jun. 3, 2025

(54) APPARATUS FOR SENSING BIOMETRIC PARAMETERS

(71) Applicant: Nokia Technologies Oy, Espoo (FI)

(72) Inventors: Akshat Agarwal, Clonmagadden (IE); Diarmuid O'Connell, Athy (IE)

(73) Assignee: Nokia Technologies Oy, Espoo (FR)

( * ) Notice: Subject to any disclaimer, the term of this patent is extended or adjusted under 35 U.S.C. 154(b) by 708 days.

(21) Appl. No.: 16/743,246

(22) Filed: Jan. 15, 2020

(65) Prior Publication Data

US 2020/0229801 A1    Jul. 23, 2020

(30) Foreign Application Priority Data

Jan. 22, 2019  (EP) ..................................... 19153041

(51) Int. Cl.
*A61B 10/00* (2006.01)
*A61B 5/00* (2006.01)

(52) U.S. Cl.
CPC ........ *A61B 10/0064* (2013.01); *A61B 5/4266* (2013.01); *A61B 5/6802* (2013.01); *A61B 2560/04* (2013.01); *A61B 2560/06* (2013.01)

(58) Field of Classification Search
CPC . A61B 10/0064; A61B 5/4266; A61B 5/6802; A61B 2560/04; A61B 2560/06; A61B 5/0533; A61B 5/01; A61B 5/14521; A61B 5/14517; A61B 5/6801; A61B 5/1491; A61M 21/02; A62B 10/0064
See application file for complete search history.

(56) References Cited

U.S. PATENT DOCUMENTS

| 4,266,556 A | 5/1981 | Barlow et al. |
| 6,160,246 A * | 12/2000 | Rock .................. D04B 1/14 219/545 |
| 7,151,062 B2 * | 12/2006 | DeAngelis ............. D03D 15/00 428/375 |
| 8,156,570 B1 * | 4/2012 | Hockaday .......... A41D 13/0025 428/154 |
| 10,470,509 B1 * | 11/2019 | Knott ................... A41D 13/002 |

(Continued)

FOREIGN PATENT DOCUMENTS

| CN | 105848564 A | 8/2016 |
| DE | 10113143 A1 | 12/2002 |

(Continued)

OTHER PUBLICATIONS

Office action received for corresponding European Patent Application No. 19153041.9, dated Nov. 12, 2021, 5 pages.

(Continued)

*Primary Examiner* — Patrick Fernandes
(74) *Attorney, Agent, or Firm* — McCarter & English, LLP

(57) ABSTRACT

Examples of the disclosure relate to an apparatus for sensing biometric parameters. The apparatus may comprise heat transfer means configured to transfer heat from a first location to a location proximate to a subject's sweat glands. The apparatus may also comprise sweat transfer means configured to transfer sweat from the location proximate to a subject's sweat glands to one or more sensors wherein the one or more sensors are configured to sense one or more biometric parameters from the subject's sweat.

20 Claims, 3 Drawing Sheets

(56) References Cited

U.S. PATENT DOCUMENTS

Figure 1:
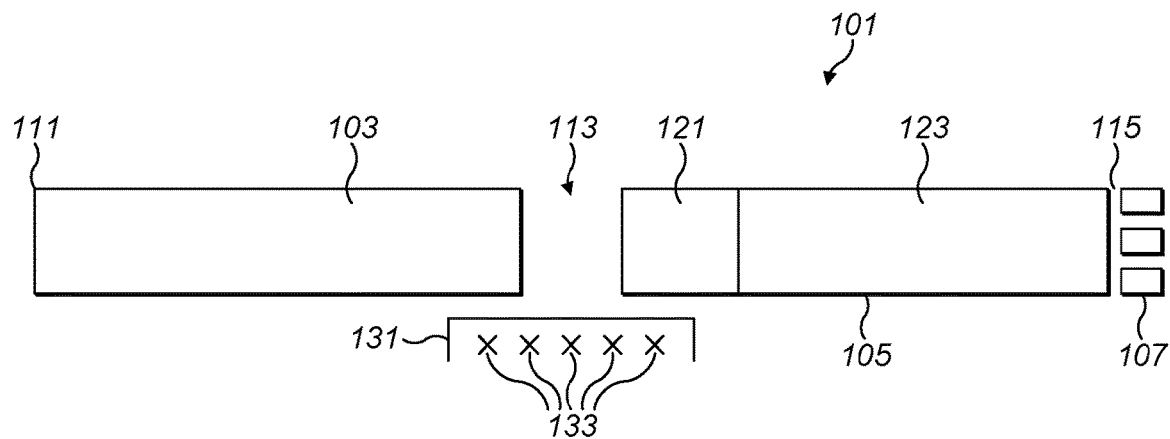

| | | | |
|---|---|---|---|
| 2013/0123570 A1* | 5/2013 | Ly | A61M 21/02 600/27 |
| 2014/0174701 A1* | 6/2014 | Kare | F28D 15/04 165/104.26 |
| 2016/0058388 A1* | 3/2016 | Kwon | A61B 5/4266 600/300 |
| 2016/0206241 A1 | 7/2016 | Cho et al. | |
| 2016/0374598 A1 | 12/2016 | Heikenfeld et al. | |
| 2017/0172227 A1* | 6/2017 | Fan | A41D 13/0025 |
| 2018/0035928 A1* | 2/2018 | Sonner | A61B 5/0533 |
| 2018/0235521 A1 | 8/2018 | Heikenfeld | |

FOREIGN PATENT DOCUMENTS

| | | |
|---|---|---|
| EP | 3415856 A1 | 12/2018 |
| EP | 3570320 A1 | 11/2019 |
| EP | 3643236 A1 | 4/2020 |
| JP | 861135646 A | 6/1986 |

OTHER PUBLICATIONS

Koh et al., "A Soft, Wearable Microfluidic Device for the Capture, Storage, and Colorimetric Sensing of Sweat", Science Translational Medicine, vol. 8, No. 366, Nov. 2016, pp. 1-13.

Schazmann et al., "A Wearable Electrochemical Sensor for the Real-time Measurement of Sweat Sodium Concentration", Analytical Methods, vol. 2, No. 4, Apr. 2010, 16 pages.

EP Application No. 18202381.2, "An Apparatus for Sensing Biometric Parameters", filed on Oct. 24, 2018, 24 pages.

Extended European Search Report received for corresponding European Patent Application No. 19153041.9, dated Jul. 18, 2019, 8 pages.

* cited by examiner

APPARATUS FOR SENSING BIOMETRIC PARAMETERS

TECHNOLOGICAL FIELD

Examples of the present disclosure relate to an apparatus for sensing biometric parameters. Some relate to an apparatus for sensing biometric parameters from a subject's sweat.

BACKGROUND

The analysis of a subject's sweat can provide information about the physical condition of the subject. Therefore it is useful to provide apparatus that are configured to sense biometric parameters from a subject's sweat.

BRIEF SUMMARY

According to various, but not necessarily all, examples of the disclosure, there is provided an apparatus comprising: heat transfer means configured to transfer heat from a first location to a location proximate to a subject's sweat glands; and sweat transfer means configured to transfer sweat from the location proximate to a subject's sweat glands to one or more sensors wherein the one or more sensors are configured to sense one or more biometric parameters from the subject's sweat.

The sweat transfer means may comprise a wicking structure.

The sweat transfer means may be configured to transfer sweat by capillary action.

The one or more sensors may be located proximate to one or more electronic components.

The one or more electronic components may comprise at least one processor configured to analyse an output signal from the one or more sensors.

The one or more sensors may be configured to sense one or more of; sweat composition, sweat rate.

The heat transfer means may be configured to transfer heat to a portion of the sweat transfer means.

The heat transfer means may comprise a heat pipe.

The first location may be a location proximate to one or more electronic components.

The first location may be a location proximate to a region of the subject's body that has a higher temperature than the location proximate to the subject's sweat glands to which the heat is transferred.

The first location may be proximate to the subject's armpit or groin.

At least one of the heat transfer means or the sweat transfer means may be formed using an additive manufacturing process.

According to various, but not necessarily all, examples of the disclosure, there is provided a wearable device comprising one or more apparatus as described above.

According to various, but not necessarily all, examples of the disclosure, there is provided a method of forming an apparatus comprising: forming heat transfer means configured to transfer heat from a first location to a location proximate to a subject's sweat glands; and forming sweat transfer means configured to transfer sweat from the location proximate to a subject's sweat glands to one or more sensors wherein the one or more sensors are configured to sense one or more biometric parameters from the subject's sweat.

At least one of the sweat transfer means and the heat transfer means may be formed using an additive manufacturing process.

At least part of the apparatus may be formed on fabric which forms part of a wearable electronic device.

At least part of the apparatus may be formed on a substrate and transferred to fabric which forms part of a wearable electronic device.

According to various, but not necessarily all, examples of the disclosure, there is provided an apparatus comprising: one or more heat transfer structures configured to transfer heat from a first location to a location proximate to a subject's sweat glands; and one or more sweat transfer structures configured to transfer sweat from the location proximate to a subject's sweat glands to one or more sensors wherein the one or more sensors are configured to sense one or more biometric parameters from the subject's sweat.

According to various, but not necessarily all, examples of the disclosure, there is provided a method of forming an apparatus comprising: forming one or more heat transfer structures configured to transfer heat from a first location to a location proximate to a subject's sweat glands; and forming one or more sweat transfer structures configured to transfer sweat from the location proximate to a subject's sweat glands to one or more sensors wherein the one or more sensors are configured to sense one or more biometric parameters from the subject's sweat.

BRIEF DESCRIPTION

Figure 2:
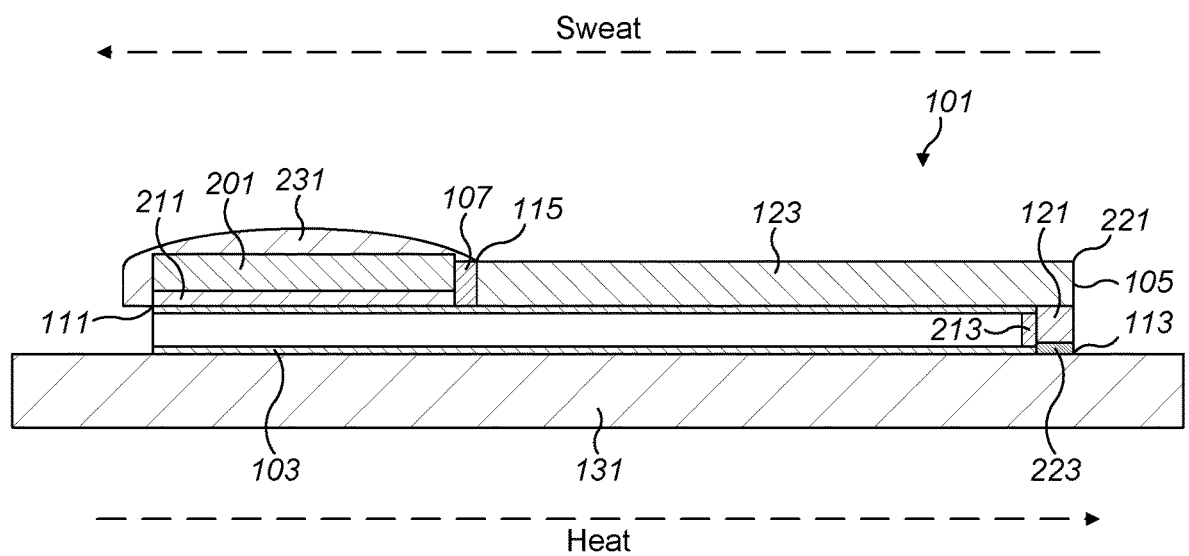
Figure 3:
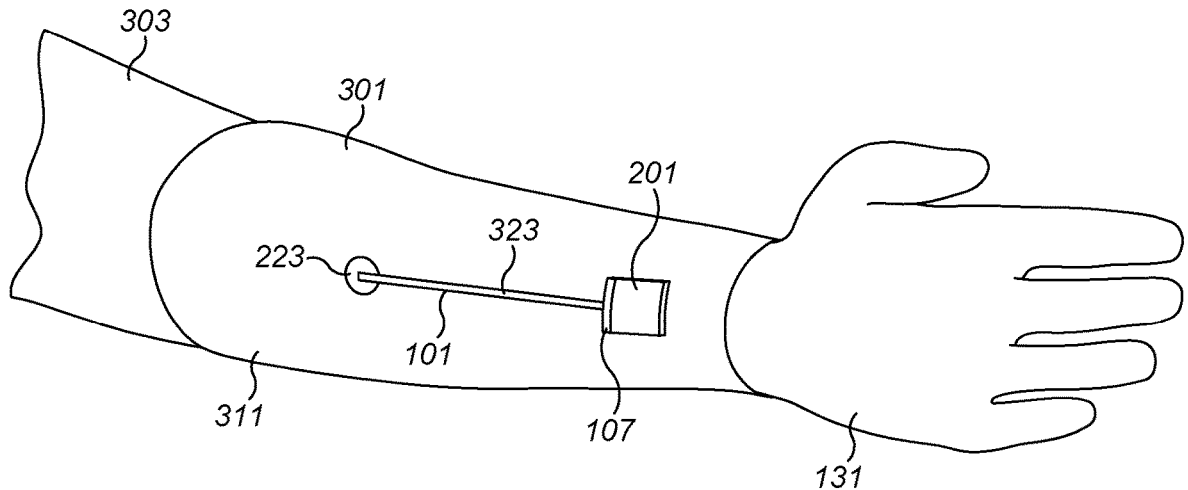
Figure 4:
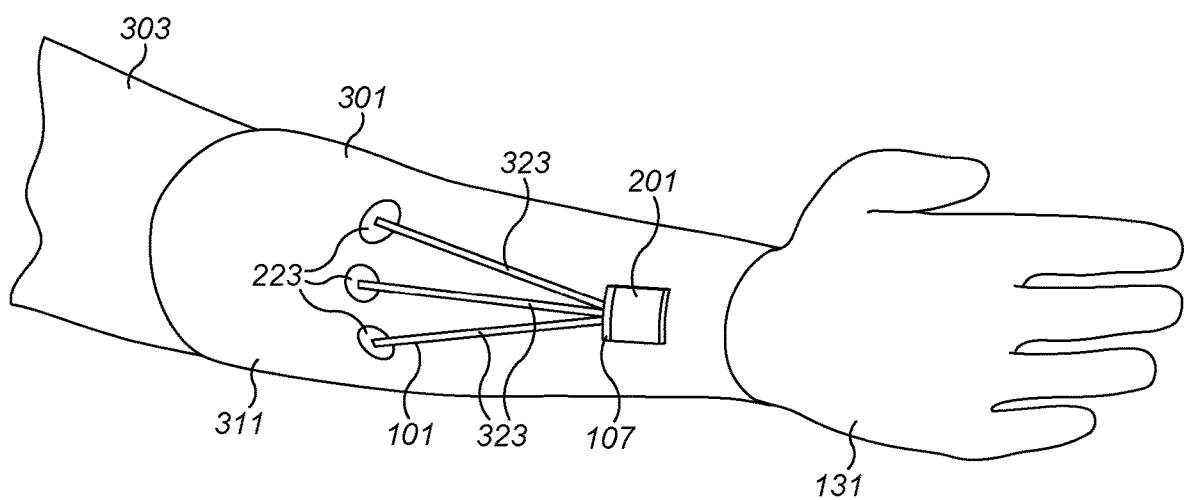
Figure 5:
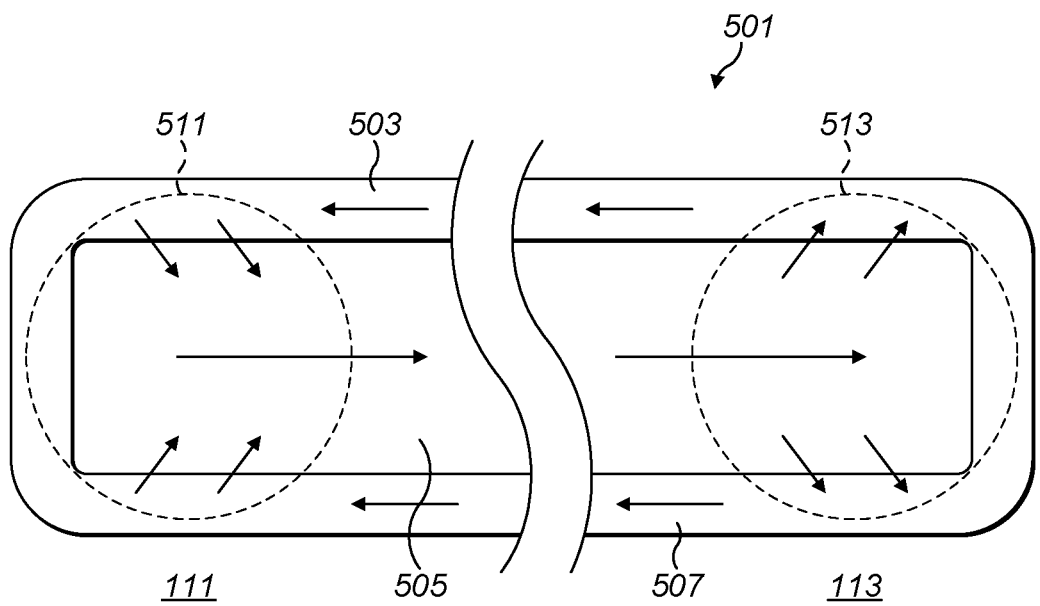
Figure 6:
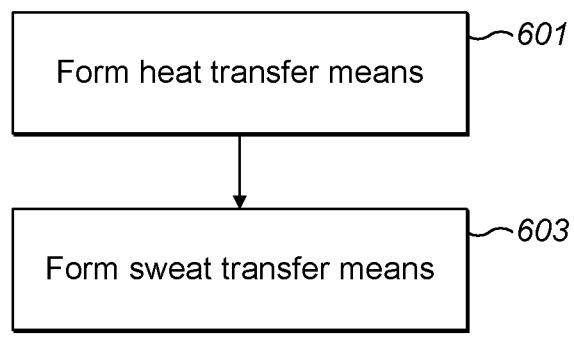

Some example embodiments will now be described with reference to the accompanying drawings in which:

FIG. 1 illustrates an example apparatus;
FIG. 2 illustrates another example apparatus;
FIG. 3 illustrates an example wearable electronic device;
FIG. 4 illustrates an example wearable electronic device;
FIG. 5 illustrates an example heat pipe; and
FIG. 6 illustrates an example method.

DETAILED DESCRIPTION

Examples of the disclosure relate to an apparatus 101 for sensing biometric parameters. The apparatus 101 may comprise heat transfer means 103 configured to transfer heat from a first location 111 to a location 113 proximate to a subject's sweat glands 133. The apparatus 101 may also comprise sweat transfer means 105 configured to transfer sweat from the location 113 proximate to a subject's sweat glands 133 to one or more sensors 107 wherein the one or more sensors 107 are configured to sense one or more biometric parameters from the subject's sweat.

The sweat transfer means 105 may enable sweat to be transferred from a location 111 proximate to a subject's sweat glands 133 to one or more sweat sensors 107 at a different location 115. This may enable the sweat sensors 107 to be positioned close to processing circuitry which may reduce the length of any routing required between the sensors 107 and the processing circuitry. In some examples it may enable the sweat sensors 107 to be positioned in a location which is more comfortable for the subject than in a location proximate to the sweat glands 133 from which sweat is collected.

The heat transfer means 103 may provide localized heating within the region of the subject's sweat glands. This localized heating may increase the generation of sweat in the region to which the heat is transferred and so may improve the efficacy of the one or more sensors 107.

FIG. 1 illustrates an example apparatus an apparatus 101 according to examples of the disclosure. The apparatus 101 comprises heat transfer means 103, sweat transfer means 105 and a plurality of sensors 107.

The heat transfer means 103 comprises any means or device which enables heat to be transferred from a first location 111 to a second location 113.

The heat transfer means 103 may comprise any suitable thermally conductive material. The thermally conductive material enables heat from the first location 111 to be transferred into the heat transfer means 103 and transferred to the second location 113. In some examples the heat transfer means 103 may comprise a metal such as copper or any other suitable material. In some examples different parts of the heat transfer means 103 may be formed from different materials. For instance a thermally conductive material could be used at the ends of the heat transfer means 103 where heat is to be exchanged but a thermally insulating material could be provided between the ends of the heat transfer means 103 to prevent the heat loss between the first location 111 and the second location 113.

In some examples the heat transfer means 103 may comprise one or more heat transfer structures such as heat pipes. An example of a heat pipe that may be used in examples of the disclosure is shown in FIG. 5. It is to be appreciated that other configurations of heat pipes could also be used in some examples of the disclosure. In other examples the heat transfer means 103 could comprise a conductive trace or any other suitable means.

In some examples the heat transfer means 103 may be flexible and/or comprise flexible portions. The heat transfer means 103 may be flexible so that the heat transfer means 103 can be easily deformed by a subject. This may enable the apparatus 101 to be integrated within a wearable electronic device. The flexibility of the heat transfer means 103 may enable a subject who is wearing the wearable device to move freely while wearing the wearable electronic device.

The heat transfer means 103 is configured to enable heat to be transferred from a first location 111 to a second location 113. The first location 111 is a region that has a higher temperature than the second location 113. One or more heat sources may be provided in the first location 111. The heat sources could comprise one or more electronic components, part of the subject's body or any other suitable source.

The electronic components that provide a heat source could comprise any electronic components which generate heat during use. The electronic components could comprise high powered electronic components. For example, the electronic components could comprise one or more processors, displays or any other suitable components. In some examples the electronic components could comprise processing circuitry which could be configured to analyse output signals from the one or more sensors 107. The electronic components could be part of the apparatus 101 or could be provided separately.

The parts of the subject's body that provide a heat source could comprise any part of the subject's body that has a higher temperature than the region proximate to the subject's sweat glands 133 to which the heat is transferred. For instance the first location 111 could be proximate to a subject's armpit or groin area. This could have a higher temperature than a region such as the subject's arm or back which may comprise the second location 113 to which the heat is transferred. A location 111 proximate to a subject's armpit or groin area could be a location which overlays the armpit or groin area or which is otherwise close enough to enable heat to be transferred from the armpit or groin area.

The second location 113 may be proximate to some sweat glands 133 of a subject 131. The second location 133 could be proximate to an area of the subject's skin in which a high concentration of sweat glands 133 can be found. The second location 113 could be proximate to a particular type of sweat gland 133. For instance in some examples the second location 113 could be proximate to eccrine sweat glands 133 while in other examples the second location could be proximate to apocrine sweat glands.

The second location 113 may be proximate to the sweat glands 133 of the subject so that heat transferred to the second location causes increased sweat production by the sweat glands 133. In some examples the second location 113 could comprise a region of skin which overlays, or at least partly overlays the sweat glands 133.

An insulating material may be provided around the heat transfer means 103 in the sections between the first location 111 and the second location 113. The insulating material may be configured to prevent heat being dissipated at locations other than the second location 113.

The heat transfer means 103 may be small to enable the heat transfer means 103 to be embedded within a wearable electronic device. In some examples the heat transfer means 103 could have a width within a range between tens of micrometers or hundreds of micrometers. The heat transfer means 103 may have a flat, or substantially flat, profile so that the heat transfer means 103 can be embedded within a wearable electronic device. The length of the heat transfer means 103 may depend on the relative location of the first location 111 and the second location 113.

The example apparatus 101 also comprises sweat transfer means 105. The sweat transfer means 105 may comprise any structures which are configured to transfer sweat from the second location 113 proximate to a subject's sweat glands 133 to one or more sensors 107. In the example shown in FIG. 1 the one or more sensors 107 are located in a third location 115 which is different to both the first location 111 and the second location 113. This means that a heat source that provides heat to the heat transfer means 103 and the one or more sensors 107 could be positioned in different locations. In other examples the one or more sensors 107 could be positioned in a location which is the same as, or close to, the first location 111 as shown in the example of FIG. 2.

The sweat transfer means 105 comprises at least one absorption region 121 and a transport region 123.

The absorption region 121 comprises a region which is configured to absorb sweat from the surface of the skin of a subject 131. In some examples the absorption region 121 may comprise an exposed wick structure. The wick structure may be positioned within the absorption region 121 so that when the sweat transfer means 105 is in use an exposed portion of the wick structure is positioned adjacent to the skin of the subject 131. The exposed wick structure may be positioned adjacent to the skin of a subject 131 so that sweat from the subject 131 can be drawn into the wick structure.

The transport region 123 extends between the at least one absorption region 121 and the one or more sensors 107. The transport region 123 also comprises a wick structure which is configured to transport sweat from the at least one absorption region 121 to the one or more sensors 107 by capillary action. In examples of the disclosure the absorption or collection of sweat by the one or more sensors 107 causes more sweat to be drawn through the wick structure in the transport region 123 and causes more sweat to be absorbed in the absorption region 121. The capillary action works without the need for any external power source and the wick structure can be configured so that, if needed, the capillary action can work against gravitational forces. This therefore enables sweat to be transferred away from the absorption region 121 to the one or more sensors 107.

In some examples the sweat transfer means 105 could comprise an impermeable coating. The impermeable coating may be provided overlaying at least part of the wick structure in the absorption region 121 and/or the transport region 123. The impermeable coating may be configured to ensure that the sweat is retained within the wick structure and does not simply evaporate straight away so that it can be transported to the one or more sensors 107. The impermeable coating may comprise any suitable material which does not allow the sweat to pass through. The impermeable coating may comprise plastics, polymer or any other suitable material.

In some examples the sweat transfer means 105 may be formed using an additive manufacturing process such as three dimensional printing. The additive manufacturing process may enable the sweat transfer structure 105 to be formed from a plurality of different materials. For instance, the wick structure and the impermeable coating could be formed from different materials.

The use of an additive manufacturing process may also enable a complex sweat transfer means 105 to be formed. For example, this may enable the sweat transfer means 105 to have multiple branches. This could enable sweat from a plurality of different locations to be transferred to a single location or sensor 107. It may also enable directional structures to be formed within the wick structure which may help to control the direction of flow of the sweat within the sweat transfer means 105.

In some examples the sweat transfer means 105 may be flexible and/or comprise flexible portions. The sweat transfer means 105 may be flexible so that the sweat transfer means 105 can be easily deformed by a subject 131. This may enable the apparatus 101 to be integrated within a wearable electronic device. The flexibility of the sweat transfer means 105 may enable a subject who is wearing the wearable device to move freely while wearing the wearable electronic device.

The sweat transfer means 105 may be small to enable the sweat transfer means 105 to be embedded within a wearable electronic device. In some examples the sweat transfer means 105 could have a width within a range between tens of micrometers or hundreds of micrometers. The sweat transfer means 105 may have a flat, or substantially flat, profile so that the sweat transfer means 105 can be embedded within a wearable electronic device. The length of the sweat transfer means 105 may depend on the relative location of the second location 113 and the one or more sensors 107.

The sensors 107 may comprise any means which may be configured to sense the sweat of a subject 131 and provide an output indicative of the sensed sweat. In some examples the sensors 107 could be configured to sense the presence of one or more analytes within the sweat, for example the sensors 107 could be configured to detect the presence of a particular chemical within the sweat. In some examples the sensors 107 could be configured to detect the sweat rate or any other suitable parameter.

The sensors 107 may comprise any material which may be configured to be sensitive to the sweat and/or an analyte within the sweat. The sensors 107 could comprise a material which has an electrical property that changes in the presence of sweat or the presence of an analyte within the sweat.

The sensors 107 may have any suitable transduction mechanism to convert the sensed sweat or analyte into an output signal. In some examples the sensors 107 may have a capacitive or a conductive transduction mechanism. If the sensors 107 have a capacitive transduction mechanism then the presence of the sweat and/or analyte may change the permittivity of the material in the sensor 107. The capacitance of the sensor 107 may have a known variation as a function of the concentration of the sweat and/or analyte. In such examples the sensors 107 may comprise a material such as polymeric material or any other suitable material.

If the sensors 107 have a conductive transduction mechanism then the presence of the sweat and/or analyte may change the conductivity of the material. The conductance of the sensor 107 may have a known variation as a function of the concentration of the sweat and/or analyte. In such examples the sensors 107 may comprise a material such as graphene oxide, graphene, functionalised graphene materials, boron nitride, molybdenite or any other suitable material.

The material which is chosen for use within the sensors 107 may depend on the analytes within the sweat that are to be detected. In some examples the same material may be used for each of the plurality of sensors 107. In some embodiments different materials may be used for different sensors 107. The use of different materials may enable different biometric parameters to be monitored.

In some examples the sensors 107 could be configured to detect biometric parameters from the subject's sweat which can be used in the diagnosis of diseases. For instance chloride concentration within sweat may be used to detect cystic fibrosis while potassium concentration within sweat may be used in the early diagnosis of cystic fibrosis and during treatment of cystic fibrosis. The concentrations of chemicals such as cadmium and lead within a subject's sweat could also be used in the diagnosis of some kidney diseases. Sweat rates and sweat composition may also be used to assist in the detection of diabetes. The presence of analytes within sweat could also be used as an indication of some types of cancer. For instance chemical compounds such as dermcidin (DCD) can be detected in sweat and are involved in tumorigenesis by promoting cell growth and survival in breast carcinomas. Prolactin inducible protein (PIP) can also be detected in sweat and is overexpressed in metastatic breast and prostate cancer. The chemical analysis of sweat may also be used to discriminate between metabolomics of patients with and without lung cancer. Other chemicals and analytes may be detected in other examples of the disclosure.

In the example apparatus 101 shown in FIG. 1 the apparatus 101 comprises three sensors 107. It is to be appreciated that the apparatus 101 could comprise any suitable number of sensors 107. In some examples the apparatus 101 could comprise only one sensor 107. In some examples the apparatus 101 could comprise a plurality of sensors 107 which could be configured to analyse sweat from different locations of the subject 131. For instance the apparatus 101 could be configured so that different sweat transfer means 105 collect sweat from different parts of the subject's body and provide these to different sensors 107. In some examples the apparatus 101 could comprise a plurality of sensors 107 where different sensors 107 are configured to detect different parameters.

In the example apparatus 101 shown in Fig.1 the heat transfer means 103 is separated from the sweat transfer means 105 so that there is no direct connection between the heat transfer means 103 and the sweat transfer means 105.

In this example heat is transferred from the heat transfer means 103 to the skin of the subject 131. This causes localised heating of the subject's skin which then increases the amount of sweat produced by the sweat glands 133. The sweat can then be removed from the subject's skin and transferred to the sensors 107 by the sweat transfer means 105.

In other examples of the disclosure the sweat transfer means 105 may be coupled to the heat transfer means 103. In some examples the sweat transfer means 105 may be coupled to the heat transfer means 103 so that there are no intervening components between the heat transfer means 103 and the sweat transfer means 105. This may enable heat to be transferred from the heat transfer means 103 to the sweat transfer means 105. For instance the heat could be transferred to the absorption region 121 of the sweat transfer means 105 rather than to the subject's skin. This heating of the sweat transfer means 105 may help to draw the liquid sweat into the sweat transfer means 105. This may also avoid over heating of the subject's skin as the heat is applied to the sweat transfer means 105 rather than directly to the skin of the subject 131.

In examples of the disclosure the sweat is collected from the subject's skin and transported to the sweat sensors 107 by the sweat transfer means 105. This enables the sweat sensors 107 to be located in any suitable location rather than requiring them to be positioned adjacent to the skin of the subject 131. In some examples the sweat sensors 107 may be located close to one or more electronic components. The electronic components could comprise processing circuitry which could be configured to analyse an output signal from the one or more sensors 107. Having the sweat sensors 107 located close to the processing circuitry may reduce the length of routing required for electrical signals within the apparatus 101 and any wearable devices comprising the apparatus 101. This may make the apparatus 101 and any wearable devices easier to manufacture. This may also reduce interference and improve the signal to noise ratio in the signal that is provided from the sensors 107 to the processing circuitry.

In addition to the benefits provided by the sweat transfer means 105 the heat transfer means 103 may be configured to provide localised heating in the second location 113. This causes more sweat to be generated in the region around the second location 113 and so increases the volume of sweat that is available to be analysed. This may increase the efficacy of the apparatus 101 for sensing parameters from the subject's sweat. This may also remove heat from unwanted locations and may help to prevent overheating in other locations.

It is to be appreciated that variations of the apparatus 101 could be provided in some examples of the disclosure. FIG. 2 illustrates another example apparatus 101 which may be provided in examples of the disclosure.

The example apparatus 101 shown in FIG. 2 also comprises heat transfer means 103, sweat transfer means 105 and one or more sensors 107. The example apparatus 101 shown in FIG. 2 also comprises one or more electronic components 201.

The electronic components 201 may provide a heat source for the heat transfer means 103. In the example shown in FIG. 2 the electronic components 201 could comprise processing circuitry which could be configured to analyse the output signals from the one or more sensors 107. Other types of electronic component may be provided in other examples of the disclosure.

A first thermal connection 211 is provided between the electronic components 201 and the heat transfer means 103. The first thermal connection 211 may comprise any means which thermally couples the electronic components 201 to the heat transfer means 103 so as to enable heat to be transferred from the electronic components 201 to the heat transfer means 103. The first thermal connection 211 could comprise any thermally conductive material such as copper.

The electronic components 201 and the thermal connection 211 are provided in a first location 111. The first location 111 is proximate to a section of the heat transfer means 103. In the example shown in FIG. 2 the first location 111 is proximate to a first end of the heat transfer means 103.

The heat transfer means 103 could comprise a heat pipe or any other suitable means. The heat transfer means 103 could be as described in relation to FIG. 1.

In the example of FIG. 2 the heat transfer means 103 also comprises a second thermal connection 213. The second thermal connection 213 enables heat to be transferred from the heat transfer means 103 to other components of the apparatus 101. The second thermal connection 213 could comprise any thermally conductive material such as copper.

The second thermal connection 213 is provided in a second location 113. The second location 113 is proximate to a different section of the heat transfer means 103 than the first location 111. In the example shown in FIG. 2 the second location 113 is provided at a second end of the heat transfer means 103.

The second thermal connection 213 is coupled to a sweat pad 223. The sweat pad 223 comprises an absorbent material which is configured to absorb sweat from the skin of the subject 131. In examples of the disclosure the sweat pad 223 may be in direct contact with the skin of the subject 131 so that there are no intervening components between the sweat pad 223 and the subject 131. This may ensure that the sweat is absorbed effectively by the sweat pad.

The second thermal connection 213 may be configured to enable heat to be transferred from the heat transfer means 103 to the sweat pad 223. This may cause localized heating of the subject 131 and increase the amount of sweat generated underneath the sweat pad 131.

In the example shown in FIG. 2 the second thermal connection 213 is also coupled to the sweat transfer means 105. The second thermal connection 213 is coupled to the absorption region 121 of the sweat transfer means 105. This enables the absorption region 121 to be heated which helps to draw sweat into the wicking structure of the sweat transfer means 105. In this example the second thermal connection 213 couples the heat transfer means 103 to the sweat transfer means 105.

The sweat transfer means 105 are also coupled to the sweat pad 223. This coupling enables sweat absorbed by the sweat pad 223 to be drawn into the sweat transfer means 105. The sweat pad 223 may be provided at a first end of the sweat transfer means 105. The first end of the sweat transfer means 105 is provided at the second location 113.

In the example of FIG. 2 the heat transfer means 103 and the sweat transfer means 105 are provided overlaying each other in a stacked configuration. In the example of FIG. 2 the sweat transfer means 105 are provided overlaying at least part of the heat transfer means 103. This may help to provide a more compact apparatus 101.

The apparatus 101 also comprises one or more sensors 107. The sensors 107 are also coupled to the sweat transfer means 105 so that sweat from the sweat transfer means 105 is provided to the sensors 107. In the example shown in FIG. 2 the sensors 107 are provided at a second end of the sweat transfer means 105. The second end of the sweat transfer means 105 is provided at a second location 115. In the example of FIG. 2 the second location 115 is proximate to the first location 111 and the one or more electronic components 201. This enables the sensors 107 to be positioned proximate to the electronic components 201 and reduces the routing required within the apparatus 101.

The sensors 107 may be positioned proximate to the electronic components 201 so that the sensors 107 are close to the electronic components 201. In some examples the sensors 107 may be positioned adjacent to the electronic components 201. In some examples the sensors 107 and the electronic components 201 could be provided on the same chip and/or circuit board.

The example apparatus 101 shown in FIG. 2 also comprises a portion of fabric 231. The portion of fabric 231 could be part of a wearable electronic device or could enable the apparatus 101 to be attached to a wearable electronic device. The electronic component 201 could be embedded within the portion of fabric 231. The portion of fabric 231 could act as a thermal insulator between the electronic component 201 and the subject 131.

The examples apparatus 101 shown in FIGS. 1 and 2 may be provided within a wearable electronic device 301. Examples of wearable electronic devices 301 which comprise apparatus 101 according to examples of the disclosure are shown in FIGS. 3 and 4.

In the example of FIG. 3 the wearable electronic device 301 comprises a sleeve 311 which is worn on the arm 303 of a subject 131. In the example of FIG. 3 the sleeve 311 is worn around the subject's lower arm 303 so that the sleeve 311 extends between the subject's wrist and the subject's elbow.

The sleeve 311 could comprise fabric. In some examples the sleeve 311 could be comprise a stretchable fabric so that the sleeve 311 fits tightly around the subject's arm 303. Other materials may be used in other examples of the disclosure.

In the example of FIG. 3 the wearable electronic device 301 comprises an apparatus 101 and one or more electronic components 201. The apparatus 101 shown in FIG. 3 comprises a sweat pad 223, a stack 323 and one or more sensors 107. The sensors 107 are provided adjacent to one or more electronic components 201.

The stack 323 comprises the heat transfer means 103 and the sweat transfer means 105. The heat transfer means 103 and the sweat transfer means 105 may be stacked overlaying each other as shown in FIG. 2 or arranged in any other suitable configuration. The stack 323 extends between the electronic components 201 and the sweat pad 223 so that heat can be transferred from the electronic component to the sweat pad 223 and so that sweat can be transferred from the sweat pad 223 to the one or more sensors 107.

The electronic component 201 is located at a first position 111 within the wearable electronic device 301. In the example wearable electronic device 301 of FIG. 3 the electronic component 201 is located so that when the wearable electronic device 301 is being worn by the subject 131 the electronic component 201 is positioned adjacent to the subject's wrist. This location could be comfortable for the subject 131. The electronic component 201 could be positioned in other locations in other examples of the disclosure.

The sweat pad 223 is at a second position 113 within the wearable electronic device 301. In the example of FIG. 3 the sweat pad 223 is located within the wearable electronic device 301 so that, when the wearable electronic device 301 is being worn by the subject 131 the sweat pad 223 is positioned close to the subject's elbow. The sweat pad 223 may be positioned in other locations in other examples of the disclosure.

The stack 323 comprising the heat transfer means 103 and the sweat transfer means 105 extends between the first location 111 which is proximate to the electronic component 201 and the second location 113 which is proximate to the sweat pad 223. This diverts heat from the area around the electronic component 201 to the area around the sweat pad 223. This provides cooling the in area around the electronic components 201 and prevents over heating around the first location 111. This also provides localised heating in the area around the sweat pad 223 so as to increase the generation of sweat and improve the efficacy of the apparatus 101. This also enables the sweat to be transferred from the sweat pad 223 to the sensors 107 which, in this example, are positioned close to the electronic components 201. This reduces the length of any electrical connections between the one or more sensors 107 and the electronic components 201 and so reduces noise in the signals that are provide to the electronic components 201.

FIG. 4 illustrates another example wearable electronic device 301. The wearable electronic device 201 shown in FIG. 4 is similar to the wearable electronic device 301 as shown in FIG. 3 in that the wearable electronic device 201 comprises a sleeve 211 which comprises an apparatus 101 and one or more electronic components 201. However in the example shown in FIG. 3 the apparatus 101 comprises a plurality of sweat pads 223 and a plurality of stacks 323 extending between the sweat pads 223 and the electronic components 201.

In the example shown in FIG. 4 the apparatus comprises three sweat pads 223. Each of the three sweat pads 223 are located within the wearable electronic device 301 so that, in use, the sweat pads 223 are located close to the subject's elbow. Having three sweat pads 223 may enable a larger volume of sweat to be collected. It may also enable sweat to be collected from different parts of the subject's body. Also this may enable heat to be transferred to different parts of the subject's body. This may reduce any overheating that could be caused by the heat generated by the electronic components.

In the example shown in FIG. 4 the apparatus 101 comprises three stacks 323 so that a stack 323 is provided to each of the sweat pads 223. Each of the stacks 323 comprises a heat transfer means 103 and a sweat transfer means 105 so as to enable heat to be transferred from the electronic component 201 to each of the sweat pads 223 and to enable sweat to be transferred from the sweat pads 323 to the one or more sensors 107.

It is to be appreciated that other configurations of wearable devices 301 could be provided in other examples of the disclosure. For instance in some examples the wearable electronic device could comprise a plurality of electronic components 201 in a plurality of different location and the heat transfer means 103 could be configured to transfer heat from the plurality of different locations to the one or more sweat pads 223 within the wearable device 103 or to any other suitable location.

FIG. 5 schematically illustrates a cross section of an example heat pipe 501 that could be used as a heat transfer means 103 in some examples of the disclosure. The heat pipe 501 comprises three layers an upper layer 503, a gas channel 505 and a lower layer 507. The upper layer 503 and the lower layer 507 provide a wick structure around the gas channel 505. The wick structure comprises a plurality of capillary channels that enable liquid to be transported along the upper layer 503 and the lower layer 507.

A working fluid is provided within the heat pipe 501. The working fluid could be water or any other suitable fluid. When the heat pipe 501 is in use the working fluid circulates through the gas channel 505 and the upper layer 503 and the lower layer 507 so as transfer heat from the first location 111 to the second location 113. When the working fluid is in the gas channel 505 the working fluid is in a gas phase and when the working fluid is in the upper layer 503 or the lower layer 507 the working fluid is in a liquid phase.

A first end of the heat pipe 501 provides an evaporator region 511 in a first location 111. The apparatus 101 may be formed so that in use the evaporator region 511 may be located in a high temperature location. The high temperature location could be proximate to an electronic component 201 or proximate to a warm part of the subject's body or any other suitable location. The first location 111 could be a high temperature location in that it is warmer than other parts of the apparatus 101 or wearable electronic device 301.

A second end of the heat pipe 501 provides a condenser region 513 in a second location 113. The apparatus 101 may be formed so that in use the condenser region 513 may be located proximate to one or more sweat glands 133 of the subject 131. The second location 113 may be a low temperature location in that it has a lower temperature than the first location 111.

At the evaporator region 511, the heat from the first location 111 causes the working fluid to evaporate and change phase from a liquid to a gas. The working fluid in the gas phase travels from the evaporator region 511 to the condenser region 513. At the condenser region 513, the comparatively cooler temperature causes the working fluid to condense and change phase from a gas to a liquid. As result, heat is moved from the evaporator region 511 in the first location 111 to the condenser region 513 in the second location 114.

At the condenser region 513, the working fluid condenses back into a liquid phase and travels back to the evaporator region 511 through capillary action of the wick structure in the upper layer 503 and the lower layer 507. Once the liquid phase working fluid has reached the evaporator region 511 again the heat at the evaporator region 511 will change the working fluid back into the gas phase. The cycle of the working fluid changing phase repeats so as to drive the working fluid in the gas phase and the heat from the evaporator region 511 to the condenser region 513.

In some examples the section of the heat pipe 501 between the evaporator region 511 and the condenser region 513 may be insulated. The insulation may help to prevent heat being lost through the heat pipe 501 to locations between the first location 111 and the second location 113.

In the example of FIG. 5 the heat pipe 501 comprises a first end and a second end where the evaporator region 511 is located at the first end and the condenser region 513 is located at the second end. In other examples the heat pipe 501 could comprise multiple branches. For instance the wearable electronic device 301 could comprise a plurality of different evaporator regions 511 which could be located at different first locations 111 within a wearable electronic device 301. As an example the wearable electronic device 301 could comprise a plurality of electronic components 201 and the heat pipe 501 could comprise a plurality of different evaporator regions 511 which may be located in proximity to the different electronic components 201.

In some examples the evaporator region 511 of the heat pipe 501 may be in the proximity of, or in direct contact with, the electronic component 201. This may help to keep the thermal resistance between the heat pipe 501 and the electronic component 201 as low as possible. For instance, the heat pipe 501 and the electronic component 201 may be encapsulated whilst in contact with one another.

In some examples the wearable electronic device 301 could comprise a plurality of different condenser regions 513 which could be located at different second locations 113 within a wearable electronic device 301. This could enable sweat to be collected from different parts of the subject's body.

In some examples the condenser region 513 of the heat pipe 501 may be in the proximity of, or in direct contact with, the skin of the subject 131. This may help to keep the thermal resistance between the heat pipe 501 and the subject 131 as low as possible to increase the localised heating of the subject 131 in the area around the sweat glands 133 from which sweat is to be collected.

FIG. 6 illustrates an example method that may be used to form apparatus 101 as described above.

The method comprises, at block 603 forming heat transfer means 103. The heat transfer means 103 are configured to transfer heat from a first location 111 to a second location 113 which, in use, is proximate to the one or more sweat glands 133 of a subject 131. The heat transfer means 103 could comprise a heat pipe 501, a thermally conductive trace or any other suitable heat transfer means.

The method also comprises, at block 603, forming sweat transfer means 105. The sweat transfer means 105 are configured to transfer sweat from a second location 113 which, in use, is proximate to the one or more sweat glands 133 of the subject 131 to one or more sensors 107 in a third location 115. The third location 115 could be a location which is proximate to one or more electronic components 201 or any other convenient location for the one or more sensors 107. In some examples different sensors 107 could be positioned in different locations.

The one or more sensors 107 are configured to sense one or more biometric parameters from a subject's sweat. The sensors 107 could comprise a material which has an electrical property that changes in the presence of sweat or the presence of an analyte within the sweat.

The heat transfer means 103 and/or the sweat transfer means 105 and/or any other suitable components of the apparatus 101 may be formed using an additive manufacturing process such as three dimensional printing. The additive manufacturing process may enable the heat transfer means 103 and/or the sweat transfer means 105 and any other suitable components of the apparatus 101 to be formed from a plurality of different materials. For instance, where the heat transfer means 103 comprises a heat pipe 501 the heat pipe 501 could comprise a thermally conductive material in the evaporator region 511 and the condenser region 513 but could also comprise a thermally insulating material in the region between the evaporator region 511 and the condenser region 513 so as to reduce heat loss.

The use of an additive manufacturing process may also enable a complex heat transfer means 103 and/or sweat transfer means 105 to be formed. For example this may enable the heat transfer means 103 to have multiple branches. This could enable heat to be transferred from a plurality of heat sources and/or may enable the heat to be transferred to a plurality of different locations. Similarly it could enable the sweat transfer means 105 to be configured to collect sweat from a plurality of different locations and/or transfer this sweat to one or more sensors 107 in a plurality of different locations.

The use of an additive manufacturing process may also enable internal structures such as wick structures for enabling capillary action to be performed.

In some examples the apparatus 101 may be formed on fabric where the fabric forms part of a wearable electronic device 301. In such examples the apparatus 101 could be formed directly onto the fabric that forms the wearable electronic device 301 so that the apparatus 101 is integrated within the wearable electronic device 301. In other examples at least part of the apparatus 101 may be formed on a substrate and transferred to fabric which forms part of the wearable electronic device 301. This process may be useful where the fabric of the wearable electronic device 3201 is not suitable for use a substrate for printing. For example, if the fabric of the wearable electronic device 301 comprises a stretchable material.

It is to be appreciated that although the blocks of the method of FIG. 6 are shown in a particular order they could be performed in any order. In some examples the blocks could be performed simultaneously. For example where the heat transfer means 103 and the sweat transfer means 105 are configured in a stack 323 the components of the stack 323 could be formed simultaneously and/or in a single process.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to 'comprising only one . . . ' or by using 'consisting'.

In this description, reference has been made to various examples. The description of features or functions in relation to an example indicates that those features or functions are present in that example. The use of the term 'example' or 'for example' or 'can' or 'may' in the text denotes, whether explicitly stated or not, that such features or functions are present in at least the described example, whether described as an example or not, and that they can be, but are not necessarily, present in some of or all other examples. Thus 'example', 'for example', 'can' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example.

Although embodiments have been described in the preceding paragraphs with reference to various examples, it should be appreciated that modifications to the examples given can be made without departing from the scope of the claims.

Features described in the preceding description may be used in combinations other than the combinations explicitly described above.

Although functions have been described with reference to certain features, those functions may be performable by other features whether described or not.

Although features have been described with reference to certain embodiments, those features may also be present in other embodiments whether described or not.

The term 'a' or 'the' is used in this document with an inclusive not an exclusive meaning. That is any reference to X comprising a/the Y indicates that X may comprise only one Y or may comprise more than one Y unless the context clearly indicates the contrary. If it is intended to use 'a' or 'the' with an exclusive meaning then it will be made clear in the context. In some circumstances the use of 'at least one' or 'one or more' may be used to emphasis an inclusive meaning but the absence of these terms should not be taken to infer and exclusive meaning.

The presence of a feature (or combination of features) in a claim is a reference to that feature or (combination of features) itself and also to features that achieve substantially the same technical effect (equivalent features). The equivalent features include, for example, features that are variants and achieve substantially the same result in substantially the same way. The equivalent features include, for example, features that perform substantially the same function, in substantially the same way to achieve substantially the same result.

In this description, reference has been made to various examples using adjectives or adjectival phrases to describe characteristics of the examples. Such a description of a characteristic in relation to an example indicates that the characteristic is present in some examples exactly as described and is present in other examples substantially as described.

Whilst endeavoring in the foregoing specification to draw attention to those features believed to be of importance it should be understood that the Applicant may seek protection via the claims in respect of any patentable feature or combination of features hereinbefore referred to and/or shown in the drawings whether or not emphasis has been placed thereon.

We claim:

1. An apparatus, comprising:
  a heat pipe having a first end and a second end and comprising a thermally conductive material at the first end and the second end and an insulating material between the first end and the second end, the heat pipe being configured to transfer heat from the first end along and in contact with a skin surface of a subject from a heat source at a first location on and in direct contact with a location on the subject's body to the second end at a second location distal to the first location and proximate to the subject's sweat glands, wherein the insulating material is configured to prevent the heat from being dissipated except at the second end; and
  a wick configured to transfer sweat from the second location proximate to the subject's sweat glands to one or more sensors at a third location distal from the first location and the second location, wherein the one or more sensors are configured to sense one or more biometric parameters from the subject's sweat.

2. An apparatus as claimed in claim 1 wherein the wick is configured to transfer sweat by capillary action.

3. An apparatus as claimed in claim 1 wherein the one or more sensors are located proximate to one or more electronic components.

4. An apparatus as claimed in claim 3 wherein the one or more electronic components comprise at least one processor configured to analyze an output signal from the one or more sensors.

5. An apparatus as claimed in claim 1 wherein the one or more sensors are configured to sense one or more of: sweat composition or sweat rate.

6. An apparatus as claimed in claim 1 wherein the heat pipe is configured to transfer heat to a portion of the wick.

7. An apparatus as claimed in claim 1 wherein the first location is a location proximate to one or more electronic components.

8. An apparatus as claimed in claim 1 wherein the first location is a location proximate to a region of the subject's body that has a higher temperature than the second location proximate to the subject's sweat glands to which the heat is transferred.

9. An apparatus as claimed in claim 1 wherein the first location is proximate to the subject's armpit or groin.

10. An apparatus as claimed in claim 1 wherein at least one of the heat pipe or the wick is formed using an additive manufacturing process.

11. A wearable electronic device comprising:
a portion of fabric;
one or more electronic components embedded in the fabric;
a heat pipe having a first end and a second end and comprising a thermally conductive material at the first end and the second end and an insulating material between the first end and the second end, the heat pipe being configured to transfer heat from the first end along and in contact with a skin surface of a subject from a heat source at a first location on and in direct contact with the subject's body to the second end at a second location distal from the first location and proximate to the subject's sweat glands, wherein the insulating material is configured to prevent the heat from being dissipated except at the second end; and
a wick configured to transfer sweat from the second location proximate to the subject's sweat glands to one or more sensors at a third location distal from the first location and the second location;
wherein the one or more sensors are configured to sense one or more biometric parameters from the subject's sweat; and
wherein the one or more sensors are located proximate to one or more electronic components.

12. An apparatus as claimed in claim 11 wherein the wick is configured to transfer sweat by capillary action.

13. An apparatus as claimed in claim 11 wherein the one or more electronic components comprise at least one processor configured to analyse an output signal from the one or more sensors.

14. An apparatus as claimed in claim 11 wherein the one or more sensors are configured to sense one or more of: sweat composition or sweat rate.

15. An apparatus as claimed in claim 11 wherein the heat pipe is configured to transfer heat to a portion of the wick.

16. An apparatus as claimed in claim 11 wherein the first location is a location proximate to one or more electronic components.

17. An apparatus as claimed in claim 11 wherein the first location is a location proximate to a region of the subject's body that has a higher temperature than the second location proximate to the subject's sweat glands to which the heat is transferred.

18. An apparatus as claimed in claim 11 wherein the first location is proximate to the subject's armpit or groin.

19. An apparatus as claimed in claim 11 wherein at least one of the heat pipe or the wick is formed using an additive manufacturing process.

20. A method, comprising:
transferring heat along a skin surface of a subject from a heat source at a first location on and in direct contact with a location on the subject's body through a heat pipe having a first end and a second end and comprising a thermally conductive material at the first end and the second end and an insulating material between the first end and the second end, the heat pipe being configured to transfer heat from the first end along and in contact with the skin surface to the second end positioned at a second location distal to the first location and proximate to the subject's sweat glands, wherein the insulating material is configured to prevent the heat from being dissipated except at the second end;
transferring sweat from the second location proximate to the subject's sweat glands through a wick to one or more sensors at a third location distal from the first location and the second location; and
sensing one or more biometric parameters from the subject's sweat using one or more sensors.

* * * * *